United States Patent [19]

Ward et al.

[11] Patent Number: 4,898,821
[45] Date of Patent: Feb. 6, 1990

[54] ANTIBIOTIC COMPOUNDS AND THEIR PREPARATION

[75] Inventors: John B. Ward, Bushey; Hazel M. Noble, Burnham; Neil Porter, Pinner; Richard A. Fletton, Ruislip; David Noble, Burnham, all of England

[73] Assignee: American Cyanamid Company, Stamford, Conn.

[21] Appl. No.: 29,885

[22] Filed: Mar. 25, 1987

Related U.S. Application Data

[62] Division of Ser. No. 775,737, Sep. 13, 1985, abandoned.

[30] Foreign Application Priority Data

Sep. 14, 1984 [GB] United Kingdom ............... 8423278
Dec. 21, 1984 [GB] United Kingdom ............... 8432519

[51] Int. Cl.$^4$ ............................................ C12P 17/18
[52] U.S. Cl. ............................................ 435/119; 435/76; 435/253.5; 435/886
[58] Field of Search ................... 435/253.5, 170, 886, 435/119, 76

[56] References Cited

U.S. PATENT DOCUMENTS 4,310,519 1/1982 Albers-Schonberg et al. ...... 435/76

FOREIGN PATENT DOCUMENTS 1390336 4/1975 United Kingdom ............... 435/253

Primary Examiner—Charles F. Warren
Assistant Examiner—Irene Marx
Attorney, Agent, or Firm—Bacon & Thomas

[57] ABSTRACT

Compounds as described having the partial formula

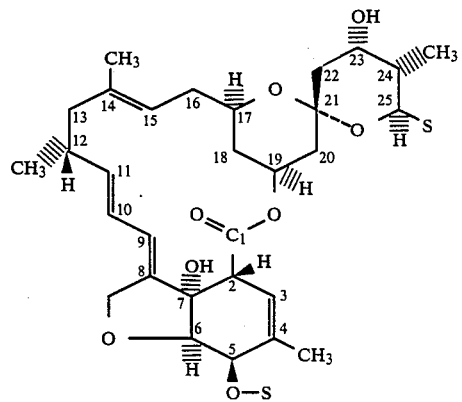

These compounds may have a 5-OH or —OMe group amd at the 25- position an isopropylene group substituted by methyl, ethyl or isopropyl.

The compounds may be used in agriculture or medicine as antiparasitics, and may be prepared by culturing certain Streptomyces strains, in particular *Streptomyces thermoarchaensis* NCIB 12015.

13 Claims, 5 Drawing Sheets

FIG. 5

FIG. 8

ANTIBIOTIC COMPOUNDS AND THEIR PREPARATION

This application is a division of application Ser. No. 775,737 filed September 13, 1985, now abandoned.

This invention relates to new antibiotic compounds and to processes for their preparation. More particularly it relates to antibiotic compounds which may be obtained by fermentation of Streptomyces organisms.

In one aspect this invention provides a novel class of substances, which we have designated Antibiotics S541, and which may be prepared by growing under controlled conditions, a previously undescribed strain of microorganism. Antibiotics S541 have antibiotic and, in particular, anti-endoparasitic, anti-ectoparasitic, antifungal, insecticidal, nematicidal and acaricidal activity and are of special interest for use in agriculture, horticulture, animal and human health. The compounds may also be of use as intermediates in the preparation of further active compounds. The compounds may be obtained by fermentation and recovered in substantially pure form as described herein.

Antibiotics S541 are a group of related compounds having the partial formula (I)

more particularly, the partial formula (II)

Six compounds having the partial formula (II) are more particularly described hereinafter.

The present invention extends to the compounds, having the above partial formula, both individually and in combination. For certain uses, for example in agriculture or horticulture, or in veterinary medicine, it may be more suitable to use Antibiotics S541 without separation into individual components, but for other uses, for example in human medicine, it may be preferable to use individual compounds. The invention thus includes a compound of the invention when in admixture with at least one other compound of the invention, and also the individual compounds for example in substantially pure form or substantially in the absence of other macrolide compounds.

Antibiotics S541 as initially isolated can readily be separated by chromatography on silica as hereinafter described into two Components having antibiotic e.g. anti-helminthic activity and which quench u.v. fluorescence at 254 nm. Component I is characterised by an Rf value in the range 0.70 to 0.75 and Component II by an Rf value in the range 0.39 to 0.46, the Rf values being determined by thin layer chromatography on Merck 5735 silica 60 plates eluting with chloroform:ethyl acetate (3:1). Components I and II (in which $R^2$ is —$CH_3$ and —H respectively) of Antibiotics S541 form a further feature of this invention.

Components I and II can themselves be further purified and have yielded six compounds of partial formula (I) possessing antibiotic e.g. anti-helminthic activity. Thus, in a further aspect of the invention we provide compounds of general formula (III)

in which $R^1$ is a methyl, ethyl or isopropyl group and $R^2$ is a hydrogen atom or a methyl group. We have designated the six compounds of formula (III) as Factor A ($R^1$=isopropyl, $R^2$=hydrogen), Factor B ($R^1$=methyl, $R^2$=methyl), Factor C ($R^1$=methyl, $R^2$=hydrogen), Factor D ($R^1$=ethyl, $R^2$=hydrogen), Factor E ($R^1$=ethyl, $R^2$=methyl) and Factor F ($R^1$=isopropyl, $R^2$=methyl). Factors A and C are particularly preferred.

Factors B, E and F are obtained from Component I, while Factors A, C and D are obtained from Component II.

The compounds of this invention have antibiotic activity e.g. antihelminthic activity, for example against nematodes, and in particular, anti-endoparasitic and anti-ectoparasitic activity. In general, the compounds are useful in combating parasites such as ectoparasites and endoparasites. Ectoparasites and endoparasites infect humans and a variety of animals and are particularly prevalent in farm animals such as pigs, sheep, cattle, goats and poultry, horses and domestic animals such as dogs and cats. Parasitic infection of livestock, leading to anaemia, malnutrition and weight loss is a major cause of economic loss throughout the world.

Examples of genera of endoparasites infecting such animals and/or humans are Ancylostoma, Ascaridia, Ascaris, Aspicularis, Bunostomum, Capillaria, Chabertia, Cooperia, Dictyocaulus, Dirofilaria, Enterobius, Haemonchus, Heterakis, Necator, Nematodirus, Nematospiroides, Nippostrongylus, Oesophagostomum, Ostertagia, Oxyuris, Parascaris, Strongylus, Strongyloides, Syphacia, Toxascaris, Toxocara, Trichonema, Trichostrongylus, Trichinella, Trichuris, and Uncinaria.

Examples of ectoparasites infecting animals and/or humans are arthropod ectoparasites such as biting insects, blowfly, fleas, lice, mites, sucking insects, ticks and other dipterous pests.

Examples of genera of such ectoparasites infecting animals and/or humans are Ambylomma, Boophilus, Coroptes, Culliphore, Damodex, Damolinia, Gastrophilus, Haematobia, Haematopinus, Haemophysalis, Hyalomma, Linognathus, Lucilia, Melophygus, Oestrus, Psorergates, Psoroptes, Rhipicephalus, Sarcoptes and Stomoxys.

The compounds according to the invention have been found to be effective both in vitro and in vivo against a range of endoparasites and ectoparasites. In particular, we have found that compounds of the invention are active against parasitic nematodes such as *Haemonchus contortus, Ostertagia circumcincta, Trichostrongylus colubiformis, Dictyocaulus viviparis, Cooperia oncophera, Ostertagia ostertagi* and *Nippostrongylus braziliensis*, and parasitic mites such as Sarcoptes sp. and Psoroptes sp.

The compounds of the invention are therefore of use in treating animals and humans with endoparasitic and/or ectoparasitic infections.

The species of the parasite will vary according to the host and the predominant site of the infection. Thus, for example *Haemonchus contortus, Ostertagia circumcincta* and *Trichostrongylus colubiformis* generally infect sheep and are predominantly located in the stomach and small intestine, whereas *Dictyocaulus viviparus, Cooperia oncophora* and *Ostertagia ostertagi* generally infect cattle and are predominantly located in the lung, intestine or stomach respectively.

Furthermore, compounds of the invention have been found to possess anti-fungal activity, for example, against strains of Candida sp. such as *Candida albicans* and *Candida glabrata* and against yeast such as *Saccharomyces carlsbergensis*.

The compounds of the invention have also been found to be active against the free living nematode *Caenorhabditis elegans*.

The compounds of the invention have also been found to be effective in combating insect, acarine and nematode pests in agriculture, horticulture, forestry, public health and stored products. Pests of soil and plant crops, including cereals (e.g. wheat, barley, maize and rice) vegetables (e.g. soya), fruit (e.g. apples, vines and citrus) as well as root crops (e.g. sugarbeet, potatoes) may usefully be treated.

In particular, we have found that the compounds of the invention are active against for example fruit mites and aphids such as *Aphis fabae, Aulacorthum circumflexum, Myzus persicae, Nephotettix cincticeps, Nilparvata lugens, Panonychus ulmi, Phorodon humuli, Phyllocoptruta oleivora, Tetranychus urticae* and members of the genera Trialeuroides; nematodes such as members of the genera Aphelencoides, Globodera, Heterodera, Meloidogyne and Panagrellus; lepidoptera such as Heliothis, Plutella and Spodoptera; grain weevils such as *Anthonomus grandis* and *Sitophilus granarius*; flour beetles such as *Tribolium castaneum*; flies such as *Musca domestica*; fire ants; leaf miners; *Pear psylla; Thrips tabaci*; cockroaches such as *Blatella germanica* and *Periplaneta americana* and mosquitoes such as *Aedes aegypti*.

According to the invention we therefore provide compounds having the partial formula (I) as defined above, which may be used as antibiotics. In particular, they can be used in the treatment of animals and humans with endoparasitic, ectoparasitic and/or fungal infections and in agriculture, horticulture, or forestry as pesticides to combat insect, acarine and nematode pests. They may also be used generally as pesticides to combat or control pests in other circumstances, e.g. in stores, buildings or other public places or location of the pests. In general the compounds may be applied either to the host (animal or human or plants or other vegetation) or to the pests themselves or a locus thereof. Particularly preferred are Factors A,B,C,D,E and F as defined above. Compounds of the invention may be formulated for administration in any convenient way for use in veterinary or human medicine and the invention therefore includes within its scope pharmaceutical compositions comprising a compound in accordance with the invention adapted for use in veterinary or human medicine. Such compositions may be presented for use in conventional manner with the aid of one or more suitable carriers or excipients.

The compositions of the invention include those in a form especially formulated for parenteral (including intramammary administration), oral, rectal, topical or implant use. When formulated in a composition that is required to be sterile, for example injections (including intramammary preparations), eye drops, ointments and implants, the active ingredient itself may have been manufactured aseptically or sterilised after manufacture by methods such as gamma-irradiation or exposure to ethylene oxide.

The compounds according to the invention may be formulated for use in veterinary or human medicine by injection and may be presented in unit dose form, in ampoules, or other unit-dose containers, or in multidose containers, if necessary with an added preservative. The compositions for injection may be in the form of suspensions, solutions, or emulsions in oily or aqueous vehicles, and may contain formulatory agents such as suspending, stabilising, solubilising and/or dispersing agents. Alternatively the active ingredient may be in sterile powder form for reconstitution with a suitable vehicle, e.g. sterile, pyrogen-free water, before use. Oily vehicles include polyhydric alcohols and their esters such as glycerol esters, fatty acids, vegetable oils such as arachis oil or cottonseed oil, mineral oils such as liquid paraffin, and ethyl oleate and other similar compounds. Other vehicles such as propylene glycol may also be used.

Compositions for veterinary medicine may also be formulated as intramammary preparations in either long acting or quick-release bases and may be sterile solutions or suspensions in aqueous or oily vehicles. The oily vehicles may for example by those described above and may also contain a thickening or suspending agent such as soft or hard paraffins, beeswax, 12-hydroxy stearin, hydrogenated castor oil, aluminium stearates, or glyceryl monostearate. Conventional non-ionic, cationic or anionic surface active agents may be used alone or in combination in the composition.

The compounds of the invention may also be presented for veterinary or human use in a form suitable for oral administration, for example in the form of solutions, syrups or suspensions, or a dry powder for constitution with water or other suitable vehicle before use, optionally with flavouring and colouring agents. Solid compositions such as tablets, capsules, lozenges, pills, boluses, powder, pastes or granules may also be used. Solid and liquid compositions for oral use may be prepared according to methods well known in the art. Such compositions may also contain one or more pharmaceutically acceptable carriers and excipients which may be in solid or liquid form. Examples of suitable pharmaceutically acceptable carriers for use in solid dosage forms include binding agents (e.g. pregelatinised maize starch, polyvinylpyrrolidone or hydroxypropyl methylcellulose); fillers (e.g. lactose, micro-crystalline cellulose or calcium phosphate); lubricants (e.g. magnesium stearate, talc or silica); disintegrants (e.g. potato starch or sodium starch glycollate); or wetting agents (e.g. sodium lauryl sulphate). Tablets may be coated by methods well known in the art. Examples of suitable pharmaceutically acceptable additives for use in liquid dosage forms include suspending agents (e.g. sorbitol syrup, methyl cellulose or hydrogenated edible fats); emulsifying agents (e.g. lecithin or acacia); non-aqueous vehicles (e.g. almond oil, oily esters or ethyl alcohol); and preservatives (e.g. methyl or propyl p-hydroxybenzoates or sorbic acid); stabilising and solubilising agents may also be included.

Pastes for oral administration may be formulated according to methods well known in the art. Examples of suitable pharmaceutically acceptable additives for use in paste formulations include suspending or gelling agents e.g. aluminium distearate or hydrogenated castor oil; dispersing agents e.g. polysorbates, non-aqueous vehicles e.g. arachis oil or oily esters; stabilising and solubilising agents. The compounds of the invention may also be administered in veterinary medicine by incorporation thereof into animals daily solid or liquid dietary intake, e.g. as part of the daily animal feed or drinking water.

For buccal administration the composition may take the form of tablets, pastes or lozenges formulated in conventional manner.

The compounds of the invention may also be administered orally in veterinary medicine in the form of a liquid drench in the form of, for example, a solution, suspension or dispersion of the active ingredient together with a pharmaceutically acceptable carrier or excipient.

The compounds of the invention may also, for example, be formulated as suppositories e.g. containing conventional suppository bases for use in veterinary or human medicine.

Compounds according to the invention may be formulated for topical administration, for use in veterinary and human medicine, as ointments, creams, lotions, powders, pessaries, sprays, dips, aerosols or drops (e.g. eye or nose drops). Ointments and creams may, for example, be formulated with an aqueous or oily base with the addition of suitable thickening and/or gelling agents. Ointments for administration to the eye may be manufactured in a sterile manner using sterilised components.

Lotions may be formulated with an aqueous or oily base and will in general also contain one or more emulsifying agents, stabilising agents, dispersing agents, suspending agents, thickening agents, or colouring agents.

Powders may be formed with the aid of any suitable powder base. Drops may be formulated with an aqueous or non aqueous base also comprising one or more dispersing agents, stabilising agents, solubilising agent or suspending agents. They may also contain a preservative.

For topical administration by inhalation the compounds according to the invention may be delivered for use in veterinary or human medicine in the form of an aerosol spray presentation or an insufflator.

The compounds of the invention may be administered in combination with other pharmaceutically active ingredients. The total daily dosages of compounds of the invention employed in both veterinary and human medicine will suitably be in the range 1–2000 $\mu$g/kg bodyweight, preferably from 10–1000 $\mu$g/kg more preferably from 100–500 $\mu$g/kg and these may be given in divided doses, e.g. 1–4 times per day.

The compounds according to the invention may be formulated in any convenient way for horticultural or agricultural use and the invention therefore includes within its scope compositions comprising a compound according to the invention adapted for horticultural or agricultural use. Such formulations include dry or liquid types, for example dusts, including dust bases or concentrates, powders, including soluble or wettable powders, granulates, including microgranules and dispersible granules, pellets, flowables, emulsions such as dilute emulsions or emulsifiable concentrates, dips such as root dips and seed dips, seed dressings, seed pellets, oil concentrates, oil solutions, injections e.g. stem injections, sprays, smokes and mists.

Generally such formulations will include the compound in association with a suitable carrier or diluent. Such carriers may be liquid or solid and designed to aid the application of the compound either by way of dispersing it where it is to be applied or to provide a formulation which can be made by the user into a dispersible preparation. Such formulations are well known in the art and may be prepared by conventional methods such as, for example by blending and/or grinding of the active ingredient(s) together with the carrier or diluent, e.g. solid carrier, solvent or surface active agent.

Suitable solid carriers, for use in formulations such as dusts, granulates and powders may be selected from for example natural mineral fillers, such as diatomite, talc, kaolinite, montmorillonite pyrophyllite or attapulgite. Highly dispersed silicic acid or highly dispersed absorbent polymers may, if desired, be included in the composition. Granulated adsorptive carriers which may be used may be porous (such as pumice, ground brick, sepiolite or bentonite) or non-porous (such as calcite or sand). Suitable pregranulated materials which may be used and which may be organic or inorganic include dolomite and ground plant residues.

Suitable solvents for use as carriers or diluents include aromatic hydrocarbons, aliphatic hydrocarbons, alcohols and glycols or ethers thereof, ester, ketones, acid amides, strongly polar solvents, optionally epoxidized vegetable oils and water.

Conventional non-ionic, cationic or anionic surface-active agents, e.g. ethoxylated alkyl phenols and alcohols, alkali metal or alkaline earth metal salts of alkyl benzene sulphonic acids, lignosulphonic acids or sulphosuccinic acids or sulphonates of polymeric phenols which have good emulsifying, dispersing and/or wetting properties may also be used either alone or in combination in the compositions.

Stabilizers, anti-caking agents, anti-foaming agents, viscosity regulators, binders and adhesives, photostabilisers as well as fertilizers, feeding stimulants or other active substances may, if desired, be included in the compositions. The compounds of the invention may also be formulated in admixture with other insecticides, acaricides and nematicides.

In the formulations, the concentration of active material is generally from 0.01 to 99% and more preferably between 0.01% and 40% by weight.

Commercial products are generally provided as concentrated compositions to be diluted to an appropriate concentration of active material for example from 0.001 to 0.0001% by weight for use.

For use in horticulture and agriculture or for use in veterinary medicine it may be desirable to use the whole fermentation broth, without separation into Components or Factors, as a source of the active compounds. It may be suitable to use dried broth (containing mycelia) or to use lysed mycelia, live or dead mycelia separated from the broth using solid/liquid separation or evaporation techniques or to use the fermentation broth remaining after separation of the mycelia. If desired the mycelia may be pasteurised or more preferably, dried e.g. by spray drying or roller drying. If desired the broth or mycelia may be formulated into compositions including conventional inert carriers, excipients or diluents as described above.

It will be appreciated from the above that in general the compounds of the invention may be used to combat infections or infestations by applying to the organism responsible for the infection or infestation or a location thereof an effective amount of one or more of said compounds.

According to a further aspect of the invention we provide a process for the production of Antibiotics S541 or a Component or Factor thereof as defined previously which comprises the step of cultivating an organism of the genus Streptomyces capable of producing at least one of the compounds of the invention whereby at least one of said compounds is produced, and if desired isolating said compound therefrom. The organism is preferably one which principally produces one or more compounds of the invention.

Based on taxonomic studies, a particular microorganism capable of producing the above substances is of a new species of the genus Streptomyces and has been named *Streptomyces thermoarchaensis*. A sample of this microorganism, which is a soil isolate, has been deposited in the permanent culture collection of the National Collections of Industrial and Marine Bacteria, Torry Research Station, Aberdeen, United Kingdom, and has been assigned the Accession number NCIB 12015. The morphological and cultural characteristics of *Streptomyces thermoarchaensis* NCIB 12015 are set forth hereinafter and this organism, together with other Antibiotics S541 roducing strains of Streptomyces, provide another feature of this invention. In particular, the invention extends to the new species of Streptomyces, the members of which possess the same essential morphological and cultural characteristics as *Streptomyces thermoarchaensis* NCIB 12015.

The invention also extends to any compounds which are capable of being produced by fermentation of *S. thermoarchaensis* NCIB 12015 and which are the optical isomers of the compounds of formula (I).

The organism of the genus Streptomyces will preferably be *Streptomyces thermoarchaensis* NCIB 12015 or a mutant thereof.

Mutants of *Streptomyces thermoarchaensis* NCIB 12015 may arise spontaneously or may be produced by a variety of methods including those outlined in Techniques for the Development of Micro-organisms by H. I. Adler in 'Radiation and Radioisotopes for Industrial Microorganisms', Proceedings of the Symposium, Vienna 1973, p241, International Atomic Energy Authority. Such methods include ionising radiation, chemical methods e.g. treatment with N-methyl-N'-nitro-N-nitrosoguanidine (NTG); heat; genetic techniques, such as recombination, transduction, transformation, lysogenisation and lysogenic conversion, and selective techniques for spontaneous mutants. Thus, for example we have obtained four mutant strains of *Streptomyces thermoarchaensis* NCIB 12015, and each of these has been deposited in the permanent culture collection of the National Collections of Industrial and Marine Bacteria, Torry Research Station, Aberdeen, United Kingdom and has been assigned the Accession number NCIB 12111, NCIB 12112, NCIB 12113 and NCIB 12114. *Streptomyces thermoarchaensis* NCIB 12111, 12112, 12113 and 12114 and mutants thereof form a further aspect of the invention.

Mutant strains NCIB 12111, 12112 and 12113 were derived by treatment of spores of *Streptomyces thermoarchaensis* NCIB 12015 with NTG and then characterised by the one-step method of Holliday (R. Holliday (1956) Nature 178 987).

Mutant strain NCIB 12114 arose by spontaneous mutation of *Streptomyces thermoarchaensis* NCIB 12015 and was identified as being resistant to streptomycin after remaining viable following exposure to 100 μg/ml of streptomycin sulphate at 28° C. for 5 days.

Taxonomic studies indicate that *Streptomyces thermoarchaensis* NCIB 12015 is a previously undisclosed microorganism of a novel species the characteristics of which are described hereinafter and are essentially those of the species as a whole. It should be understood that the invention extends to all members of this species including any organism having substantially similar essential characteristics.

On the preferred sporulation media, oatmeal agar, malt-yeast agar and inorganic salts-starch agar (Shirling, E. B. and Gottlieb, D. (1966) Int. J. Syst. Bacteriol. 16, 313–340), *Streptomyces thermoarchaensis* NCIB 12015 grows abundantly producing a stable substrate mycelium and an aerial mycelium bearing spores in open spiral chains as side branches off the main hyphae. On these media the reverse pigmentation is yellow/brown and the sporophores are grey. At ×100 magnification, sporophores contain 2–5 turns per chain with 5–10 spores within each turn of the spiral. On average, sporophores contain between 20 and 50 spores. Scanning electron microscopy at a magnification ×12000 reveals the spores to be smooth walled and ellipsoidal in shape with dimensions of 0.7 μm × 1.4 μm at their widest points. *Streptomyces thermoarchaensis* NCIB 12015 is gram-positive and is able to grow and sporulate at temperatures between 20° C. and 50° C.

A comparison of the foregoing data with published descriptions in Bergey's Manual of Determinative Bacteriology (Eighth Edition) indicates that the organism *Streptomyces thermoarchaensis* NCIB 12015 belongs to the genus Streptomyces.

Identification of *Streptomyces thermoarchaensis* NCIB 12015 to species-group level was carried out using a computerised identification matrix reported by Williams et al (J. Gen. Microbiol (1983) 129, 1815–1830). The results of the 41 taxonomic tests described by the above authors are as follows for *Streptomyces thermoarchaensis* NCIB 12015:

| CHARACTER | RESULT |
|---|---|
| Spore chain verticillati | − |
| Spore chain retinaculiaperti | − |
| Spore chain rectiflexibiles | − |
| Spore chain spirales | + |
| Fragmentation of mycelium | − |
| Spore surface smooth | + |
| Spore surface rugose | − |
| Spore colour grey | + |
| Spore colour red | − |
| Spore colour green | − |
| Reverse yellow/brown | + |
| Reverse red/orange | − |
| Melanin production | − |
| Use of adonitol | − |
| Use of cellobiose | + |
| Use of D-fructose | + |
| Use of meso-inositol | − |
| Use of inulin | + |
| Use of mannitol | − |
| Use of raffinose | + |
| Use of rhamnose | + |
| Use of D-xylose | + |
| Use of DL-α-aminobutyric acid | − |
| Use of L-histidine | + |
| Use of L-hydroxyproline | − |
| Degradation of allantoin | + |
| Degradation of arbutin | + |
| Degradation of xanthine | + |
| Degradation of pectin | + |
| Degradation of lecithin | − |
| Nitrate reduction | + |
| Hydrogen sulphide production | + |
| Tolerance of sodium azide (0.01%, w/v) | − |
| Tolerance of sodium chloride (7%, w/v) | − |
| Tolerance of phenol (0.1%, w/v) | + |
| Growth at 45° C. | + |
| Resistance to neomycin (50 $\mu g.ml^{-1}$) | − |
| Resistance to rifampicin (50 $\mu g.ml^{-1}$) | + |
| Antibiosis to *Aspergillus niger* LIV 131 | + |
| Antibiosis to *Bacillus subtilis* NC1B 3610 | − |
| Antibiosis to *Streptomyces murinus* ISP 5091 | + |

The organism was not identified as belonging to any of the 23 major species groups (Williams, S. T. et al. (1983) J. Gen. Microbiol 129, 1815–1830) or any of the minor species groups and single member clusters defined by Williams and co-workers (J. Gen. Microbiol (1983) 129, 1743–1813). The characteristics of *Streptomyces thermoarchaensis* NCIB 12015 were also compared with descriptions of known Streptomyces species in Bergey's Manual of Determinative Bacteriology (Eighth Edition), in ISP reports by Shirling and Gottlieb (Int. J. Syst. Bacteriol. (1968) 18, 69–189; Int. J. Syst. Bacteriol. (1968) 18, 279–392; Int. J. Syst. Bacteriol (1969). 19, 391–512; Int. J. Syst Bacteriol (1972) 22, 265–394) and with new species validly described in the International Journal of Systematic Bacteriology since 1980.

No match could be made between *Streptomyces thermoarchaensis* NCIB 12015 and a described species and on this basis we believe that *Streptomyces thermoarchaensis* NCIB 12015 is the first known member of a new species belonging to the genus Streptomyces.

Mutant strains NCIB 12111, 12112, 12113 and 12114, all have substantially similar essential characteristics to *Streptomyces thermoarchaensis*. However, NCIB 12111 requires adenine for growth, NCIB 12112 requires serine for growth, NCIB 12113 requires histidine for growth, and NCIB 12114 is resistant to streptomycin.

The production of S541 by fermentation of a suitable Streptomyces organism may be effected by conventional means i.e. by culturing the Streptomyces organism in the presence of assimilable sources of carbon, nitrogen and mineral salts.

Assimilable sources of carbon, nitrogen and minerals may be provided by either simple or complex nutrients. Sources of carbon will generally include glucose, maltose, starch, glycerol, molasses, dextrin, lactose, sucrose, fructose, carboxylic acids, amino acids, glycerides, alcohols, alkanes and vegetable oils. Sources of carbon will generally comprise from 0.5 to 10% by weight of the fermentation medium. will generally include glucose, maltose, starch, glycerol, molasses, dextrin, lactose, sucrose, fructose, carboxylic acids, amino acids, glycerides, alcohols, alkanes and vegetable oils. Sources of carbon will generally comprise from 0.5 to 10% by weight of the fermentation medium.

Sources of nitrogen will generally include soya bean meal, corn steep liquors, distillers solubles, yeast extracts, cottonseed meal, peptones, ground nut meal, malt extract, molasses, casein, amino acid mixtures, ammonia (gas or solution), ammonium salts or nitrates. Urea and other amides may also be used. Sources of nitrogen will generally comprise from 0.1 to 10% by weight of the fermentation medium.

Nutrient mineral salts which may be incorporated into the culture medium include the generally used salts capable of yielding sodium, potassium, ammonium, iron, magnesium, zinc, nickel, cobalt manganese, vanadium, chromium, calcium, copper, molybdenum, boron, phosphate, sulphate, chloride and carbonate ions.

An antifoam may be present to control excessive foaming and added at intervals as required.

Cultivation of the Streptomyces organism will generally be effected at a temperature of from 20° to 50° C. preferably from 25° to 40° C., especially around 34° C., and will desirably take place with aeration and agitation e.g. by shaking or stirring. The medium may initially be inoculated with a small quantity of a suspension of the sporulated microorganism but in order to avoid a growth lag a vegetative inoculum of the organism may be prepared by inoculating a small quantity of the culture medium with the spore form of the organism, and the vegetative inoculum obtained may be transferred to the fermentation medium, or, more preferably to one or more seed stages where further growth takes place before transfer to the principal fermentation medium. The fermentation will generally be carried out in the pH range 5.5 to 8.5, preferably 5.5 to 7.5.

The fermentation may be carried out for a period of 2–10 days, e.g. about 5 days.

Where it is desired to separate material containing Antibiotics S541 and any components or factors thereof from the whole fermentation or to isolate any of the components or factors this may be carried out by conventional isolation and separation techniques. Antibiotics S541 according to the invention are predominantly contained in the mycelia of the cells, but may also be found in the fermentation broth and, the isolation techniques may also be applied to the fermentation broth either before or after clarification. It will be appreciated that the choice of isolation techniques may be varied widely.

Antibiotics S541 may be isolated and separated by a variety of fractionation techniques, for example adsorption-elution, precipitation, fractional crystallisation and solvent extraction which may be combined in various ways.

Solvent extraction and chromatography and fractional crystallisation have been found to be most suitable for isolating and separating the compounds of the invention.

Following the fermentation, the mycelia may be harvested using conventional techniques, for example, filtration or centrifugation. Thereafter, for example, the material may be extracted from the mycelia with an appropriate organic solvent such as ketone. e.g. acetone, methylethyl ketone or methylisobutyl ketone; a hydrocarbon, e.g. hexane; a halogenated hydrocarbon e.g. chloroform, carbontetrachloride or methylene chloride; an alcohol, e.g. methanol or ethanol; or a diol, e.g. propane 1,2-diol; or an ester, e.g. methyl acetate or ethyl acetate. It will be appreciated that if the mycelia contain significant amounts of water, it will be preferable to use a water-soluble solvent.

Generally, more than one extraction is desirable to achieve optimum recovery. Preferably the first extraction is carried out using a water miscible solvent such as methanol or acetone. The antibiotics may be recovered as a crude extract by removal of the solvent. The solvent extracts may themselves be extracted, if desired after reduction of the solvent volume, for example by evaporation. At this stage it is preferable to use a water-immiscible solvent such as hexane, chloroform, methylene chloride or ethyl acetate or mixtures thereof, sufficient water being added to achieve satisfactory partition of the antibiotic compounds. Removal of the water-immiscible phase yields a material containing Antibiotics S541. If desired Factor B may be separated by crystallisation from an appropriate solvent e.g. isopropanol.

Purification and/or separation of the active components and/or factors (completely or from other macrolide compounds present) may be effected by conventional techniques such as for example, chromatography (including high performance liquid chromatography) on a suitable support such as silica, a non-functional macroreticular adsorption resin for example cross linked polystyrene resins such as Amberlite XAD-2, XAD-4 or XAD-1180 resins (Rohm & Haas Ltd), or an S112 resin (Kastell Ltd) or on an organic solvent-compatible cross-linked dextran such as Sephadex LH20 (Pharmacia UK Ltd), or, in the case of hplc, reverse phase supports such as hydrocarbon linked silica e.g. $C_{18}$-linked silica. The support may be in the form of a bed, or more preferably packed in a column. In the case of non-functional macroreticular resins such as XAD-1180 or S112, mixtures of organic solvents such as acetonitrile with water may be used for elution.

A solution of the compounds in a suitable solvent will generally be loaded on to the silica or Sephadex columns, if desired after first reducing the volume of solvent. The column may optionally be washed and then eluted with a solvent of suitable polarity. In the case of Sephadex and silica, alcohols, such as methanol; hydrocarbons, such as hexane; acetonitrile; halogenated hydrocarbons, such as chloroform or methylene chloride; or esters, such as ethyl acetate, may be used as solvents. Combinations of such solvents either alone or with water may also be used.

Elution and separation/purification of the compounds of the invention may be monitored by conventional techniques such as chromatography e.g. thin layer chromatography and high performance liquid chromatography or by utilising the properties of the compounds described previously.

Chromatography over silica, preferably using an eluant such as chloroform:ethyl acetate, readily separates Antibiotics S541 into Components I and II, Component I being eluted first. Factors B, E and F can then readily be obtained from Component I using chromatography e.g. high performance liquid chromatography. Similarly Factors A, C and D may readily be isolated from Component II. Alternatively, Factor B can be separated from Factors E and F by crystallisation from an alcohol such as methanol or iso-propanol. The mother liquors containing Factors E and F may, if desired, be subjected to further purification e.g. chromatography over silica and Factors E and F isolated using high performance liquid chromatography. Once obtained, the Factors may be further purified by crystallisation e.g. from methanol, iso-propanol or a methanol/water mixture, and the invention extends to compounds according to the invention in crystalline form.

By a suitable combination of the foregoing procedures, the compounds according to the invention have been isolated as solids. It will be appreciated that the order in which the above purification steps are carried out and the choice of those which are used may be varied widely.

Thus, Factor B has been obtained as a crystalline solid having a purity in excess of 90%. Similarly, Factors A, C, D, E and F have also been obtained having a purity in excess of 90%. The Factors may, however, be used, as described above, at levels of purity appropriate to their intended use. For use in human medicine, purities of at least 90%, preferably greater than 95%, are desirable. For veterinary or agricultural or horticultural use, lower purities will suffice, for example 50% or lower.

The following Examples illustrate the invention. The following abbreviations are used: tlc - thin layer chromatography (using Merck 5735 silica 60 plates and developed with $CHCl_3$:ethyl acetate (3:1) unless otherwise specified); CCM - column chromatography using Merck 7734 silica 60 (200×4 cm column unless otherwise specified) packed and eluted with $CHCl_3$:ethyl acetate (3:1) unless otherwise specified; hplc - high performance liquid chromatography; PE - petroleum ether (b.p. 60°–80° C. unless otherwise specified); L - liter; EA - ethyl acetate. Media A, B and C referred to in the Examples are:

| Medium A | |
|---|---|
| | $gL^{-1}$ |
| D-Glucose | 15.0 |
| Glycerol | 15.0 |
| Soya Peptone | 15.0 |
| NaCl | 3.0 |
| $CaCO_3$ | 1.0 |

Distilled water to 1 liter, pH adjusted to pH 7.0 with aqueous NaOH before autoclaving.

| Medium B | |
|---|---|
| | $gL^{-1}$ |
| D-Glucose | 2.5 |
| Malt dextrin MD 30E (Roquette (UK)Ltd) | 25.0 |
| Arkasoy 50 (British Arkady Co.Ltd) | 12.5 |

-continued

| Medium B | |
|---|---|
| | gL$^{-1}$ |
| Molasses | 1.5 |
| K$_2$HPO$_4$ | 0.125 |
| Calcium carbonate | 1.25 |
| MOPS (3-(N—morpholino)propane-sulphonic acid) | 21.0 |

Distilled water to 1 liter, pH adjusted to 6.5 with 5N NaOH before autoclaving.

| Medium C | |
|---|---|
| | gL$^{-1}$ |
| D-Glucose | 2.5 |
| Malt dextrin MD 30E (Roquette (UK) Ltd) | 25.0 |
| Arkasoy 50 | 12.5 |
| Beet Molasses | 1.5 |
| K$_2$HPO$_4$ | 0.125 |
| CaCO$_3$ | 1.25 |
| Silicone 1520 (Dow Corning) | 0.625 |

Distilled water to 1 liter, pH adjusted to 6.5 before sterilisation.

EXAMPLE 1

Spores of *Streptomyces thermoarchaensis* NCIB 12015 were inoculated onto agar slants made up of the following ingredients:

| | gL$^{-1}$ |
|---|---|
| Yeast extract (Oxoid L21) | 0.5 |
| Malt extract (Oxoid L39) | 30.0 |
| Mycological Peptone (Oxoid L40) | 5.0 |
| Agar No. 3 (Oxoid L13) | 15.0 |

Distilled water to 1 liter, pH approximately 5.4 and incubated at 28° C. for 10 days. The mature slant was then covered with a 10% glycerol solution (6 ml) and scraped with a sterile tool to loosen the spores and mycelium. 0.4 ml aliquots of the resulting spore suspension were transferred to sterile polypropylene straws which were then heat-sealed and stored in liquid nitrogen vapour until required.

The contents of a single straw were used to inoculate 10 ml of Medium A which was then incubated at 28° C. for 3 days on a shaker rotating at 250 rpm with a 50 mm diameter orbital motion. This incubated medium was used to inoculate at a level of 2%, 15 tubes and two 250 ml Erlenmeyer flasks containing 10 ml and 50 ml respectively of Medium B.

The tubes and flasks were grown at 28° C. for 5 days, and the cultures were then filtered separately under vacuum and the cells shaken for 30 minutes with a volume of methanol equal to that of culture filtrate.

Activity against *Caenorhabditis elegans* was detected in extracts of cells grown in both tubes and flasks and these mycelial extracts were bulked, evaporated to dryness and re-extracted with methanol to a concentrate (6 ml) which was applied to a column of Sephadex LH20 (110×2.5 cm) packed and eluted with methanol. 10 ml Fractions were collected.

Fractions 21–28 were pooled and evaporated to yield an oily residue (156 mg) which was extracted with CHCl$_3$:EA (3:1) to give an extract (3 ml) which was subjected to CCM (55×2.5 cm column) 10 ml Fractions were collected and analysed by tlc using plates containing fluorescent indicator. Fractions 20 to 23 and Fractions 36 to 44 gave rise to two major areas which quenched the fluorescence and which we have identified as Component I (Rf 0.70) and Component II (Rf 0.43). Evaporation of fractions 20–23 yielded Component I as a solid (9 mg) $\lambda_{max}$238 nm, E$_1$1340; $\lambda_{max}$245 nm, E$_1$1350; and $\lambda_{max}$254 nm, E$_1$1200. Evaporation of fractions 36 to 44 yielded Component II as a solid (11 mg) $\lambda_{max}$238 nm, E$_1$1440; $\lambda_{max}$245 nm, E$_1$1460; and $\lambda_{max}$254 nm, E$^1$280.

EXAMPLE 2

Two 250 ml Erlenmeyer flasks containing 50 ml of Medium A were each inoculated with 0.2 ml of a spore suspension of *Streptomyces thermoarchaensis* NCIB 12015 taken from a straw prepared as described in Example 1. The flasks were incubated at 28° C. for 3 days on a shaker rotating at 250 rpm with a 50 mm diameter orbital motion and the contents of both flasks were then used to inoculate a 20 L fermenter vessel containing Medium B (12 L). The culture was harvested after 5 days growth and processed as described in Example 3.

EXAMPLE 3

Fermentation broth (12 L) obtained as described in Example 2 was harvested after 5 days growth at 28° C. and centrifuged (4,200 rpm at 10° C. for 15 min). The cell pellet was mixed with methanol (5 L) and allowed to stand for 20 hours at 4° C. The mycelial extract was filtered, evaporated at 40° C. and subjected to azeotropic distillation after addition of butan-1-ol (100 ml). The extract was then treated with methanol (5×200 ml) and the combined extracts were evaporated to 100 ml and applied to a column of Sephadex LH20 (112×5 cm). The column was eluted with methanol and after a forerun of 200 ml, 50 ml fractions collected. Fractions 40–90 were pooled and evaporated to yield an oily residue (3.85 g). The residue was extracted with 77 ml of CHCl$_3$:EA (3:1), filtered and then subjected to CCM approximately 15 ml fractions being collected after a forerun of 200 ml.

Fractions 124 to 142 containing Component I were pooled and evaporated to yield a solid (253 mg) of which 216 mg were purified by hplc (Zorbax ODS, 25×2.1 cm, 80% CH$_3$CN/H$_2$O). Fractions 250 to 320 containing Component II were pooled and evaporated to yield a solid (602 mg) of which 540 mg were purified by hplc (as for fractions 124–142) and fractions from several runs were collected.

Material eluting from the hplc column was monitored by uv spectroscopy at 243 nm. Peaks absorbing at this wavelength were dried down and (i) tested for activity against *Caenorhabditis elegans* and (ii) analysed by tlc. Four peaks which were active against *Caenorhabditis elegans* also had an Rf value in the range 0.39 to 0.46 or 0.70 to 0.75.

Component I gave one peak with an Rf value of 0.70 to 0.75 and this peak has been assigned as Factor B. Component II gave three peaks with an Rf value of 0.39 to 0.46 and these peaks have been assigned as Factors A, C and D.

Factor A eluted from the hplc column between 260 to 340 ml after the injection of the sample and had an Rf value of 0.44 by tlc. Factor B eluted from the hplc column between 270 to 310 ml after the injection of the sample and had an Rf value of 0.72 by tlc. Factor C eluted from the hplc column between 160 to 180 ml after the injection of the sample and had an Rf value of 0.4 by tlc. Factor D eluted from the hplc column between 220 to 250 ml after the injection of the sample and had an Rf value of 0.42 by tlc. The further characteristics of Factors A, B, C and D are described hereinafter.

EXAMPLE 4

0.4 ml of a spore suspension of organism *Streptomyces thermoarchaensis* NCIB 12015 taken from a straw prepared as described in Example 1 was used to inoculate a 250 ml Erlenmyer flask containing Medium A (50 ml). The flask was incubated at 28° C. for 4 days on a shaker rotating at 250 rpm with a 50 mm diameter orbital motion. Portions (8 ml) were then used to inoculate each of two 2l flat-bottomed flasks, each containing 400 ml of the same medium, before incubation under the same conditions for 3 days.

The contents of both flasks were then used to inoculate a fermenter vessel (70 L) containing Medium B (40 L) supplemented with Silicone 525 [Dow-Corning; 0.0625% (v/v)]. The fermentation was carried out with agitation and aeration sufficient to maintain a dissolved oxygen level of greater than 20% of saturation, with Silicone antifoam added as required. The fermentation was harvested after 10 days, and the broth (40 L) was clarified by centrifugation (15000 r.p.m). The residual supernatant was displaced with water (5 L), and the recovered cells (1.4 kg) were frozen at −20°.

After a week the frozen cells were thawed, suspended in methanol (15 L) and stirred gently for 15 h. The suspension was then filtered and the solid residue was re-extracted with methanol (10 L). The combined filtrate (25 L) was diluted with water (12 L) and extracted with PE (25 L). After 30 min the phases were separated by centrifugation.

The lower, methanol phase was re-extracted three times with PE (25 L, 15 L and 15 L). The combined PE phases (80 L) were concentrated by three passes through a Pfaudler 8.8-12V-27 wiped-film evaporator (Vapour pressure 0.1 bar, vapour temperature 20°, steam temperature 127°), and the concentrate (8 L) was dried with sodium sulphate (1 kg) and further concentrated under reduced pressure at 40° in a rotary film evaporator. The oily residue (15 ml) was dissolved in a mixture of $CHCl_3$ and EA (70 ml, 3:1 v/v) and subjected to CCM, fractions of approximately 40 ml being collected after a forerun of 1,400 ml.

Figure 1:
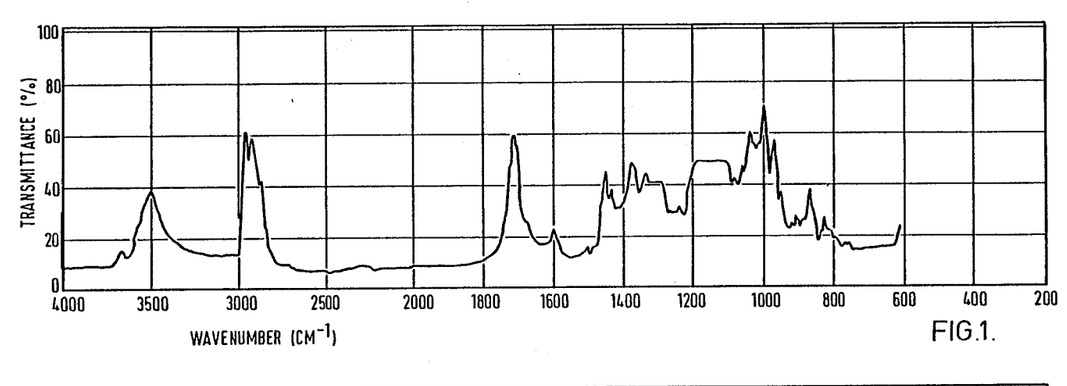
Figure 2:
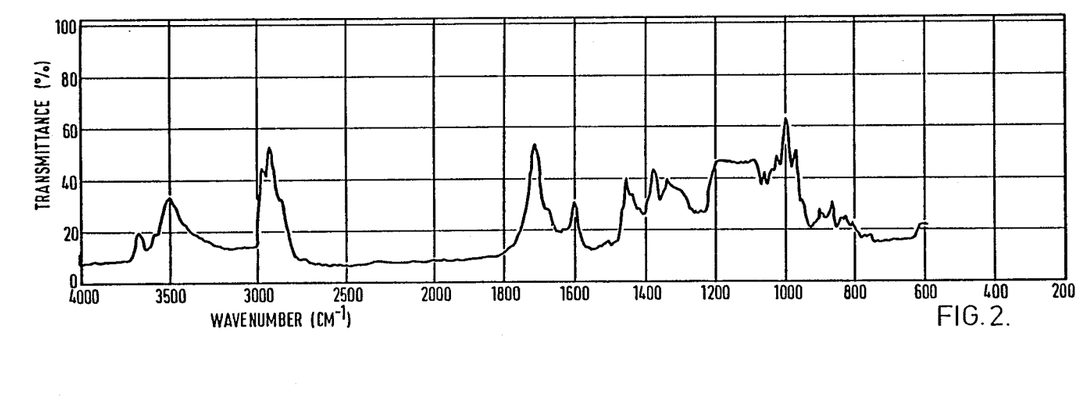
Figure 3:
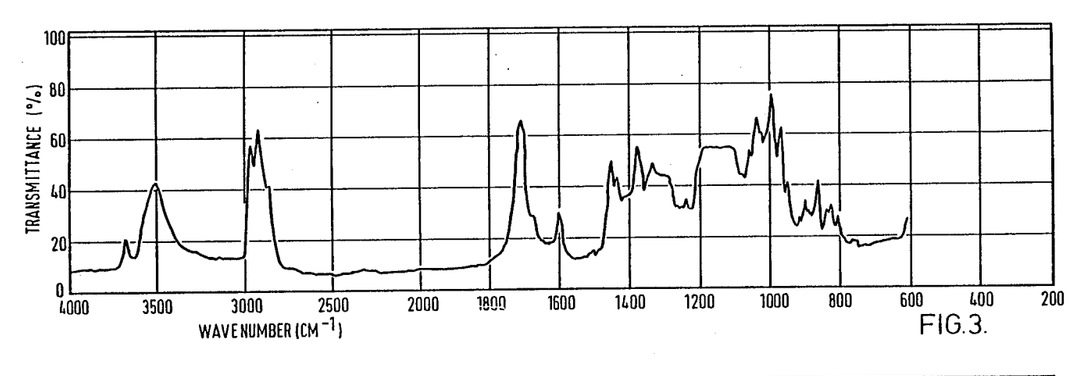
Figure 4:
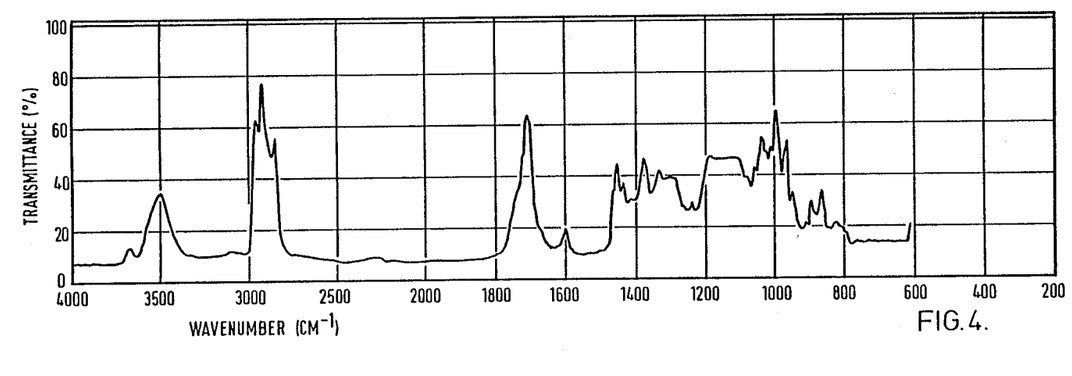
Figure 5:
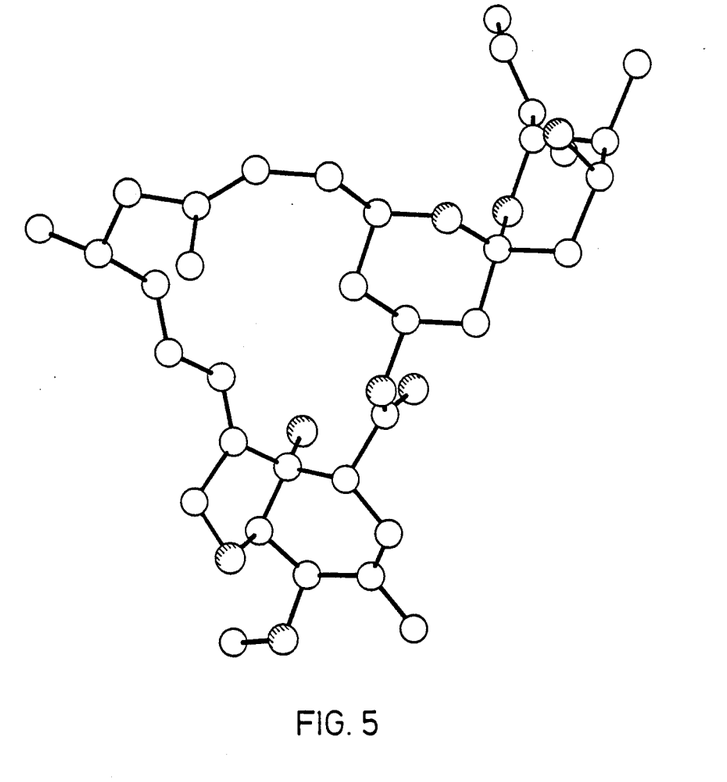
Figure 6:
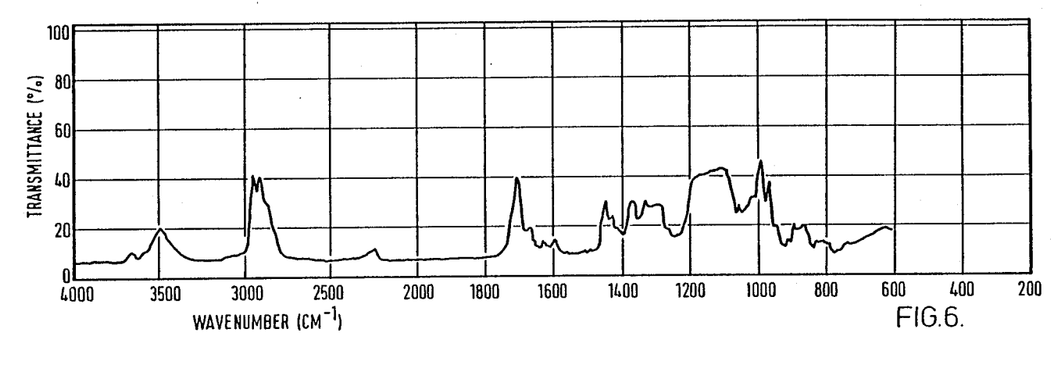
Figure 7:
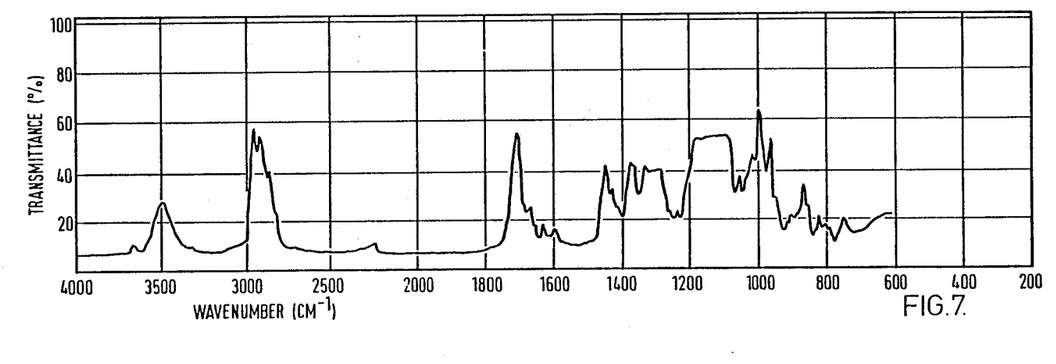

Fractions 45-65 were combined and evaporated to yield Factor B (940 mg; as defined in Example 3), which was crystallised twice from methanol and finally from nitromethane. The crystals were submitted for single crystal X-ray diffraction analysis, which showed that they were orthorhombic, clear prisms with a=10.171(3), b=13.317(5), c=25.032(7)Å, V=3391 Å$^3$, Z=4, space group $P2_12_12_1$, $D_c$=1.18 gcm$^{-3}$, R=0.053 for 2169 independent observed reflections ($\theta$<58°) measured on a diffractometer with Cu-K$\alpha$ radiation ($\lambda$=1.54178 Å). The structure as determined by X-ray crystallography is shown in FIG. 5.

EXAMPLE 5

An inoculum of *Streptomyces thermoarchaensis* NCIB 12015 was prepared as described in Example 4 with the growth period being two days, and used to inoculate a fermenter vessel (70 L) containing Medium B (40 L) supplemented with polypropylene 2000 (0.06% v/v) instead of Silicone 525. Polypropylene 2000 was added as required throughout the fermentation to control foaming. The fermentation was carried out at 28° C., with agitation and aeration sufficient to maintain a dissolved oxygen level of greater than 30% saturation. After 24 hours of fermentation, a portion of broth (9 L) was transferred to a fermenter (700 L) containing medium (450 L) made up as follows:

| | gL$^{-1}$ |
|---|---|
| D-glucose | 2.8 |
| Malt Dextrin (MD30E) | 27.8 |
| Arkasoy 50 | 13.9 |
| Molasses | 1.7 |
| $K_2HPO_4$ | 0.14 |
| $CaCO_3$ | 1.39 |
| Silicone 525 (Dow Corning) | 0.06% (v/v) |

Adjusted to pH 6.5 before sterilisation.

The fermentation was carried out at 28° C. with agitation and aeration sufficient to maintain a dissolved oxygen level of greater than 20% saturation. Polypropylene 2000 antifoam was added as required. After 2 days the pH was controlled to 7.2 with the addition of $H_2SO_4$. The fermentation was harvested after 5 days.

The broth (450 L) was clarified by centrifugation and the residual supernatant was displaced with water (20 L). The recovered cells (25.5 kg) were stirred for 1 hour in sufficient methanol to give a total volume of 75 L. The suspension was filtered and the solid residue was re-extracted with methanol (35 L) and filtered. The combined filtrate (87 L) was diluted with water (40 L) and extracted with PE. After 30 min. the phases were separated by centrifugation and the lower methanol phase was re-extracted with PE (30 L) after the addition of water (40 L). After separation the lower phase was again extracted with PE (30 L). The combined PE phases (85 L) were concentrated by three passes through a Pfandler 8.8-12v-27 wiped-film evaporator (vapour pressure 0.1 bar, vapour temperature 20°, steam temperature 127°). The concentrate (9 L) was dried with sodium sulphate (2 kg) and further concentrated under reduced pressure at 40° in a rotary film evaporator. The oily residue (130 g) was dissolved in $CHCl_3$ to give 190 ml and this was subjected to CCM [column packed and washed (500 ml) in $CHCl_3$] fractions of approximately 40 ml being collected after a forerun of 1,400 ml.

Fractions 32-46 were combined and evaporated to yield an oil (21.2 g). Fractions 47-93 were combined and evaporated to give an oil (20.1 g) which was dissolved in $CHCl_3$:EA (3:1) to 50 ml, and subjected to CCM, fractions of approximately 40 ml being collected after a forerun of 1,400 ml. Fractions 22-36 were combined and evaporated to give an oil (3.1 g) which was added to the oil obtained from fractions 32-46 from the first column. The combined oils were dissolved in boiling methanol (4 ml) which was then added to hot propan-2-ol (20 ml) to yield on standing crystalline Factor B (2.57 g).

Mother liquor after crystallisation of Factor B was evaporated to yield an oil which was dissolved in an equal volume of $CH_2Cl_2$ and loaded onto a column (30×2.2 cm) of Merck Kieselgel 60 (70–230 mesh ASTM, Art. No. 7734) packed in $CH_2Cl_2$. The bed was washed with $CH_2Cl_2$ (2 bed volumes) and eluted with $CHCl_3$:EA (3:1) (2 bed volumes). Evaporation of the eluate yielded an oil which was dissolved in methanol and subjected to preparative hplc on Spherisorb S5 ODS-2 (250 mm×20 mm, Phase Sep. Ltd.). The sample (5 ml) was pumped onto the column over a period of 1 minute and the column was eluted with acetonitrile:water (7:3) under the following conditions:

| Time (mins) | Flow (ml/min) | |
|---|---|---|
| 0.00 | 0.00 | Injection time |
| 1.00 | 0.00 | |
| 1.10 | 30.00 | |
| 39.90 | 30.00 | |
| 40.00 | 35.00 | |
| 75.00 | 35.00 | |

Material eluting from the hplc column was monitored by uv spectroscopy at 238 nm. Evaporation of the combined fractions with peaks eluting at 26.3 minutes yielded Factor E as a solid. Evaporation of the combined fractions with peaks eluting at 36.4 minutes yielded Factor F as a solid. The further characteristics of Factors E and F are described hereinafter.

EXAMPLE 6

Fermentation broth (similar to that prepared in Example 2) harvested after 117 hr was autoclaved (121° C., 1 hr), cooled to room temperature and stirred on a magnetic stirrer to give a homogeneous suspension of cells. Two portions (2 ml) were centrifuged (12,000 g, 2 min., room temperature), the supernatants were decanted and the residual cells were suspended in water (2 ml), thoroughly mixed and subjected to centrifugation again (12,000 g., 2 min., room temperature). After decantation of the supernatants, the cells were washed twice more with distilled water (2 ml portions). The washed cells were then thoroughly mixed with either water (2 ml) or methanol (2 ml) and left at room temperature with occasional shaking for 1.5 hr. The suspensions were again centrifuged (12,000 g, 2 mins, room temperature) and the supernatants were sequentially diluted in water. The cells from the aqueous suspension were re-suspended in water and immediately sequentially diluted in water. Portions (10 μl) of each of the dilutions were added to a suspension (200 μl) of the nematode *Caenorhabditis elegans* in a buffer solution containing $Na_2HPO_4$ (6 g/L), $K_2HPO_4$ (3 g/L), NaCl (5 g/L) and $MgSO_4.7H_2O$ (0.25 g/L) and adjusted to pH 7.0. After 4 hr the nematode suspensions were examined to find which dilutions of test mixture caused total inhibition of motility in greater than 98% of the nematodes in the assay suspension. It was found that 1 in 5, 1 in 25, 1 in 250 and 1 in 500 dilutions of the methanol extract, 1 in 5, 1 in 25, 1 in 250, 1 in 500 and 1 in 1000 dilutions of the cell suspension and 1 in 2, 1 in 4 and 1 in 8 dilutions of the aqueous extract caused such inhibition of the nematodes when 10 μl were added to 200 μl of nematode suspensions.

EXAMPLE 7

250 ml Erlenmyer flasks containing either 50 ml of Medium A or 50 ml of Medium B were inoculated with 0.4 ml of a spore suspension of *Streptomyces thermoarchaensis* NCIB 12015 taken from a straw prepared as described in Example 1. The flasks containing Medium A or Medium B were incubated at 28° for 2 days on a rotary shaker operating at 250 rev/min with a 50 mm diam. throw. Portions (8 ml) from each medium were then used to inoculate 2 liter flat-bottomed flasks containing 400 ml of the same medium (A or B respectively). These flasks were incubated under the same conditions for two days.

Two 70 L fermenters were each inoculated with 2 flasks of Medium A and one other 70 L fermenter was inoculated with two flasks of Medium B. Each Fermenter contained 40 L of Medium C.

The fermentations were carried out at 34°, with agitation and aeration sufficient to maintain a dissolved oxygen level greater than 30% of saturation. After approximately 24 h of fermentation the pH ws controlled to 7.2 with the addition of aqueous $H_2SO_4$. Polypropylene glycol 2000 antifoam was added as required. After 5 days, these fermentations were harvested and bulked.

One other 70 L fermenter, which was also inoculated with two flasks containing Medium B, contained Medium B supplemented with silicone 1520 (0.06%). The fermentation was carried out at 28° with agitation and aeration sufficient to maintain a dissolved oxygen level of greater than 30% of saturation. Polypropylene glycol 2000 was added as required to control foaming. After 24 hours, a 9 L portion was transferred to a 700 L fermenter containing 450 L of Medium C.

The fermentation was carried out at 34° C. with agitation and aeration sufficient to maintain a dissolved oxygen level of greater than 30% of saturation. Foaming was controlled by the addition of polypropylene glycol 2000 and after approximately 24 hours the pH was controlled to 7.2 with the addition of aqueous $H_2SO_4$. The fermentation was harvested after 4 days and bulked with the three 40 L fermentations described above.

The bulked harvest broths were centrifuged through a Sharples AS16PY at about 120 L/h. The residual supernatant in the centrifugal bowl was displaced with water.

The recovered cells (11.65 kg) were emulsified in methanol (33 L) with a Silverson mixer. After 60 min the suspension was filtered through a twill cloth and the residue was once again emulsified in methanol (34 L). After 40 min the suspension was again filtered. The filtrates from the two methanol extractions were combined.

The combined extracts (53.5 L) were mixed with water (27 L) and PE (27 L). After stirring for 20 min the two phases were separated on a Westfalia MEM 1256 centrifuge. The lower aqueous methanol phase (70 L) was mixed with water (37 L) and PE (27 L) and stirred and separated as before. The interfacial emulsion in the PE phase was broken with acetone (4 L). The lower aqueous methanol phase (108 L) was then mixed with water (40 L) and PE (27 L) for a third time, and stirred and separated as before, with acetone (4 L) being used to clear the interfacial emulsion. The three hexane extracts were then combined.

The combined PE extract (85 L) was concentrated with a wiped film evaporator (vapour pressure 0.15 bar, vapour temperature 26°). The concentrate (3 L) was dried with sodium sulphate (2 kg) and then further evaporated under reduced pressure at 40°. The resultant oil (639 g) was dissolved in 300 ml of a mixture of chloroform and EA (3:1 v/v) and filtered and washed through glass fibre paper. The filtrate and washings (1060 ml) were subjectd to CCM (1500 mm × 100 mm diam) with elution at a flow rate of 6 L/h.

The fraction eluting between 8.8 and 13.1 L was bulked and evaporated at low pressure to an oil (56.3 g), while that eluting between 13.1 L and 24.6 L was similarly reduced at low pressure to a pale yellow solid (153.4 g). The early fraction was shown to contain largely Factor B while the later fraction contained a mixture of Factors A, B, C and D. The Factor B in this later fraction was progressively removed by repeating the chromatography CCM as described above, twice-the last time on fresh silica-under similar conditions except that the flow rate was reduced to 3 L/h.

The peaks containing Factors A, C and D from the second of these columns eluted between 8.8 and 17.6 L, the residual Factor B which it contained being separated in the third column from which Factors A, C and D eluted between 14 and 28 L. This final bulked eluate was reduced at low pressure to a solid (114 g). The peaks containing Factor B from the two columns (7.5-8.8 L and 10.3-13.4 L respectively) were evaporated to oils (10.7 g and 10 g respectively) and were combined with the oil obtained from the first of the three columns.

The oils containing Factor B were dissolved in boiling methanol (25 ml) and mixed with boiling propan-2-ol (100 mL). On cooling to 4° Factor B crystallised. It was filtered off, washed with methanol (200 mL), cooled to −20°, and dried under vacuum to give 25.3 g of Factor B.

The solid from the third silica column which contained Factors A, C and D was dried under vacuum to constant weight (87 g). Samples (20 g) of this solid were dissolved in methanol (190 mL) and made up to 230 mL with 7:3 (v/v) acetonitrile:water. Portions (5 mL) of the solution were then chromatographed on a column (250 mm×21.2 mm diam) of spherisorb ODS-2 (5 μm particle diam), with 7:3 acetonitrile water as the eluting solvent. The flow rate was held at 20 mL/min for about 10 sec; it was then steadily increased over a 22 min period to 34 mL/min, and was held at this rate for a further 3 min. The eluting factors were detected at 238 nm. Factor C eluted between 11.0 and 13.4 min, Factor D between 13.4 and 17.4 min and Factor A between 17.4 and 23.0 min.

The fractions containing Factor C from each chromatographic separation were bulked and reduced at low pressure to a solid. Fractions containing Factor A were similarly reduced to a solid. Fractions containing Factor D were also bulked and reduced to an impure solid (7 g). This was redissolved in methanol (65 mL), mixed with 7:3 acetonitrile water and rechromatographed on the spherisorb ODS2 column as already described except that the flow was kept constant at 20 mL/min throughout. The Factor D now eluted between 16 and 20 min, and this fraction was bulked from each chromatographic run. The bulked eluate was reduced to a solid. The three solids containing Factors A, C and D were dried over $P_2O_5$ under vacuum to constant weight (55 g, 7.0 g and 1.21 g respectively).

The four solids isolated from this process were each shown to be similar to authentic samples of Factors A, B, C and D.

EXAMPLE 8

250 ml Erlenmyer flasks containing 50 mL of medium B were inoculated with 0.5 ml of a spore suspension of each of *Streptomyces thermoarchaensis* NCIB 12111, 12112, 12113 and 12114 taken from straws prepared as described in Example 1.

Flasks containing *Streptomyces thermoarchaensis* NCIB 12111, NCIB 12112 and NCIB 12113 were incubated at 31° C. on a rotary shaker. The flask containing *Streptomyces thermoarchaensis* NCIB 12114 was incubated at 28° C. for 2 days and then 1 mL of broth was transferred to another 250 ml Erlenmyer flask containing 50 mL of medium B. This flask was incubated at 31° C. on a rotary shaker. All flasks were shaken at 250 rev/min with a 50 mm diameter throw.

After 4 days incubation, a 10 mL sample of each broth was centrifuged at 1,250 g for 45 minutes, and processed as follows. The supernatant was discarded and the pellet resuspended to 10 mL in methanol. The suspension was shaken vigorously and left for 1 hour with occasional mixing. The suspension was then centrifuged at 10,000 g for 5 minutes and the supernatant analysed by hplc (S5 ODS-2, 10 cm×4.6 mm, 70% $CH_3CN/0.1M$ $NH_4H_2PO_4$). Peaks were monitored at 246 nm.

Analysis by hplc showed the presence of Factors A, B, C and D in each case.

EXAMPLE 9

Factors A, B, C, D, E and F have been found to have the following characteristics:

(i) They contain carbon, hydrogen and oxygen only.
(ii) Electron Impact (E.I.) mass spectroscopy of Factors A, B, C, D, E and F gave the following results:

| Factor | molecular ion | corresponding to molecular formula |
|---|---|---|
| A | 612.37 | $C_{36}H_{52}O_8$ |
| B | 598.35 | $C_{35}H_{50}O_8$ |
| C | 584.34 | $C_{34}H_{48}O_8$ |
| D | 598.35 | $C_{35}H_{50}O_8$ |
| E | 612.3638 | $C_{36}H_{52}O_8$ |
| F | 626.3807 | $C_{37}H_{54}O_8$ |

Fast Atom Bombardment (FAB) mass spectroscopy gave the following results:

| Factor | +ve FAB | −ve FAB | mol. wt. |
|---|---|---|---|
| A | M/Z 635[M + Na]+<br>M/Z 613[M + H]+ | M/Z 611[M − H]− | 612 |
| B | M/Z 691[M + H + glycerol]+<br>M/Z 599[M + H]+<br>M/Z 581[MH − $H_2O$]+<br>M/Z 563[MH − $2H_2O$]+ | | 598 |
| C | M/Z 607[M + Na]+ | M/Z 583[M − H]− | 584 |
| D | M/Z 621[M + Na]+ | M/Z 597[M − H]− | 598 |

Field desorption mass spectroscopy of Factor E gave the following result M/Z 612 M+, and of Factor F gave the result M/Z 626 M+.

An E.I. spectrum of Factor A with accurate mass measurement gave ions at 612.37 $C_{36}H_{52}O_8$; 466.31 $C_{30}H_{42}O_4$; 448.30 $C_{30}H_{40}O_3$; 425.23 $C_{26}H_{33}O_5$; 354.22 $C_{23}H_{30}O_3$; 297.22 $C_{21}H_{29}O$; 278.11 $C_{15}H_{18}O_5$; 247.17 $C_{16}H_{23}O_2$; 219.18 $C_{15}H_{23}O$; 95.05 $C_6H_7O$.

An E.I. Spectrum of Factor B with accurate mass measurement gave ions at 598.35 $C_{35}H_{50}O_8$; 438.28 $C_{28}H_{38}O_4$; 420.26 $C_{28}H_{36}O_3$; 314.19 $C_{20}H_{26}O_3$; 248.14 $C_{15}H_{20}O_3$; 151.08 $C_9H_{11}O_2$.

An E.I. spectrum of Factor C with accurate mass measurement gave ions at: 584.34 $C_{34}H_{48}O_8$; 566.33 $C_{34}H_{46}O_7$; 438.28 $C_{28}H_{38}O_4$.

An E.I. spectrum of Factor D with accurate mass measurement gave ions at: 598.35 $C_{35}H_{50}O_8$; 452.29 $C_{29}H_{40}O_4$; 434.28 $C_{29}H_{38}O_3$.

An accurate mass measurement of Factor E in the E.I. ionisation mode gave an ion at: 452.2908 $C_{29}H_{40}O_4$; and for Factor F an ion at: 466.3067 $C_{30}H_{24}O_4$.

(iii) Factors A, B, C, D, E and F have characteristic IR spectra in bromoform including the following peaks: For Factor A at about 3510 (OH), 1712 (ester) and 998 cm$^{-1}$ (C—O); For Factor B at about 3510 (OH), 1710 (ester) and 996 cm$^{-1}$ (C—O); For Factor C including peaks at about 3510 (OH), 1712 (ester) and 996 cm$^{-1}$ (C—O); For Factor D including peaks at about 3508 (OH), 1711 (ester) and 996 cm$^{-1}$ (C—O); For Factor E including peaks at about 3500 (OH), 1708 (ester) and 994 cm$^{-1}$ (C—O); and for Factor F including bands at about 3500 (OH), 1708 (ester), and 997 cm$^{-1}$ (C—O).

The full spectra for Factors A, B, C, D, E and F are shown in FIGS. 1,2,3,4,6 and 7 respectively of the accompanying drawings.

(iv) Factors A, B, C, D, E and F have a UV spectrum in methanol (c=0.002%) showing the following (where I=inflexion and M=maximum):

| Factor | λ(nm) | | $E_1^1$ | Factor | λ(nm) | | $E_1^1$ |
|---|---|---|---|---|---|---|---|
| A | 252 | (I) | 318 | D | 252 | (I) | 263 |
|  | 244.5 | (M) | 468 |  | 244.5 | (M) | 393 |
|  | 239 | (I) | 430 |  | 239 | (I) | 362 |
| B | 252 | (I) | 302 | *E | 252 | (I) | 266 |
|  | 244.5 | (M) | 426 |  | 244 | (M) | 402 |
|  | 239 | (I) | 394 |  | 238 | (M) | 373 |
| C | 252 | (I) | 316 | *F | 252 | (I) | 285 |
|  | 244.5 | (M) | 470 |  | 244.5 | (M) | 421 |
|  | 239 | (I) | 432 |  | 239 | (M) | 389 |

(*methanol c = 0.001%)

It should be noted that while the λ$_{max}$ values above are characteristic of each Factor, the $E_1^1$ values reflect the purity of the material as it has been obtained. However, the ratios of the $E_1^1$ values are characteristic of the compound per se.

(v) A 200 MHz proton nmr spectrum of solution of each Factor in deutero-chloroform includes signals [τ values with multiplicities, coupling constants (Hz) and integration values in parentheses] centred at about:

Factor A: 4.1 to 4.4(m,2H); 4.61(broad s,1H); 4.6 to 4.75(m,2H); 4.81(d,9,1H); 5.05(m,1H); 5.34(s,2H); 5.69(d,5,1H); 6.06(d,5,1H); 6.17(m,1H); 6.26(d,11,1H); 6.37(m,1H); 6.46(d,10,1H); 6.74(q,2,1H); 7.42(m,1H); 7.7 to 7.9(m,5H); 8.14(s,3H); 8.40(s,3H); 8.47(s,3H); 8.61(t,11,1H); 8.96(d,7,3H); 9.06(d,7,3H); 9.02(d,7,3H); 9.13(q,11,1H); 9.21(d,7,3H).

Factor B: 4.2 to 4.4(m,2H); 4.55(q,7,1H); 4.65(broad,s,1H); 4.6 to 4.8(m,2H); 5.06(m,1H); 5.3 to 5.5(m,2H); 6.01(d5,1H); 6.07(d,5,1H); 6.12(s,1H); 6.24(d,11,1H); 6.24(m,1H); 6.3 to 6.5(m,2H); 6.53(s,3H); 6.73(q,2,1H); 7.62(m,1H); 7.6–8.0(m,4H); 8.22(s,3H); 8.35(d,7,3H); 8.41(s,3H); 8.49(s,3H); 8.62(t,11,1H); 9.03(d,6,3H); 9.12(q,11,1H); 9.22(d,7,3H).

Factor C: 4.29(d,11,t,2,1H); 4.4 to 4.6(m,3H); 4.56(broad s,1H); 5.14(dd,15,10,1H); 5.23(m,1H); 5.65(broad s,2H); 5.72(d,6,1H); 5.95(d,10,1H); 5.99(d,6,1H); 6.08(broad s,1H); 6.1 to 6.4(m,3H); 6.62(q,3,1H); 7.7 to 8.1(m,ca7H); 8.18(s,3H); 8.33(s,3H); 8.48(d,7,3H); 8.64(s,3H); 8.68(t,11,1H); 9.00(d,7,3H); 9.08(d,7,3H); 9.12(q,12,1H).

Factor D: 4.18 to 4.4 (m,2H); 4.47 to 4.81 (m,4H); 5.04 (m,1H); 5.35 (s,2H); 5.72 (d,7,1H); 6.07 (d,7,1H); 6.15 to 6.45 (m,4H); 6.74 (q,4,1H); 7.45–8.1 (m,8H); 8.16 (s,3H); 8.41 (s,3H); 8.49 (s,3H); 8.62 (t,11,1H); 8.92–9.05 (m,6H); 9.21 (d,7,3H).

Factor E: 4.1 to 4.3 (m,2H); 4.5 to 4.8 (m,4H total); 5.04 (m,1H); 5.2 to 5.5 (m,2H); 6.01 (d,5,1H); 6.05 (d,5,1H); 6.11 (s,1H); 6.1 to 6.4 (m,3H); 6.45 (d,10,1H); 6.51 (s,3H); 6.70 (q,2,1H); 7.60 (m,1H); 8.20 (s,3H); 8.41 (s,3H); 8.47 (s,3H); 8.60 (t,11,1H); 9.00 (t,7,3H); 9.02 (d,6,3H); 9.11 (q,11,1H); 9.20 (d,7,3H).

Factor F: 4.2 to 4.4 (m,2H); 4.62 (s,1H); ca 4.70 (m,2H); 4.80 (d,9,1H); 5.04 (m,1H); 5.2 to 5.5 (m,2H); 5.99 (d,5,1H); 6.05 (d,5,1H); 6.11 (s,1H); 6.1 to 6.3 (m,2H); ca 6.36 (m,1H); 6.45 (d,10,1H); 6.51 (s,3H); 6.70 (q,2,1H); 7.42 (m,1H); 7.58 (m,1H); 8.19 (s,3H); 8.40 (s,3H); 8.47 (s,3H); 8.60 (t,11,1H); 8.95 (d,7,3H); 9.05 (d,7,3H); 9.01 (d,7,3H); 9.10 (q,11,1H); 9.21 (d,6,3H).

(vi) A noise-decoupled 25.05 MHz carbon-13 nmr spectrum of a solution of each factor in deutero-chloroform include peaks [δ values with multiplicities of signals in off-resonance spectrum in parentheses] at about:

Factor A: 173.2(s); 142.6(d); 139.2(s); 137.6(s); 137.1(s); 137.0(d); 130.4(s); 123.1(d); 120.1(d); 117.8(d); 99.5(s); 80.0(s); 79.0(d); 76.5(d); 69.0(d); 68.3*; 67.4(d); 48.2(t); 45.5(d); 40.9(t); 40.5(t); 35.8*; 34.5(t); 22.1(q); 34.5(t); 26.6(d); 22.6(q); 22.0(q); 19.7(q); 15.3(q); 13.7(q); 10.8(q).

Factor B: 173.4(s); 142.1(d); 139.5(s); 137.1(s); 135.7(s); 133.7(s); 123.6(d); 123.3(d); 120.0(d); 119.3(d); 118.2(d); 99.5(s); 80.1(s); 77.3(d); 76.6(d); 76.4(d); 69.0(d); 68.3(d); 67.9 *; 67.6 *; 57.5(q); 48.2(t); 45.4(d); 40.7(t); 40.5(t); 35.8*; 34.5(t); 22.1(q); 19.6(q); 15.3(q); 13.6(q); 12.9(q); 10.5(q).

Factor C: 173.3(s); 142.2(d); 140.3(s); 138.5(s); 137.0(s); 134.9(s); 123.9(d); 121.1(d); 120.6(d); 118.1(d); 100.2(s); 80.6(s); 80.1(d); 77.4(d); 69.2(d); 69.0(d); 68.3 *; 68.0(d); 67.9(d); 48.6(t); 46.3(d); 41.4(t); 36.5 *; 36.3 *; 36.1(d); 35.0(t); 22.6(q); 20.0(q); 15.4(q); 14.3(q); 13.1(q); 10.8(q).

Factor D: 173.2 (s); 142.5 (d); 139.1 (s); 137.5 (s); 137.1 (s); 132.1 (s); 131.4 (d); 123.1 (d); 120.1 (d); 117.8 (d); 99.5 (s); 79.9 (s); 79.2 (d); 76.5 (d); 69.0 (d); 68.3*; 68.1*; 67.6*; 67.4 *; 48.2 (t); 45.5 (d); 40.8 (t); 40.5 (t); 35.7 *; 34.5 (t); 22.0 (q); 20.6 (t); 19.6 (q); 15.3(q); 13.7 (q); 13.6 (q); 10.7 (q). * multiplicity uncertain.

Figure 8:
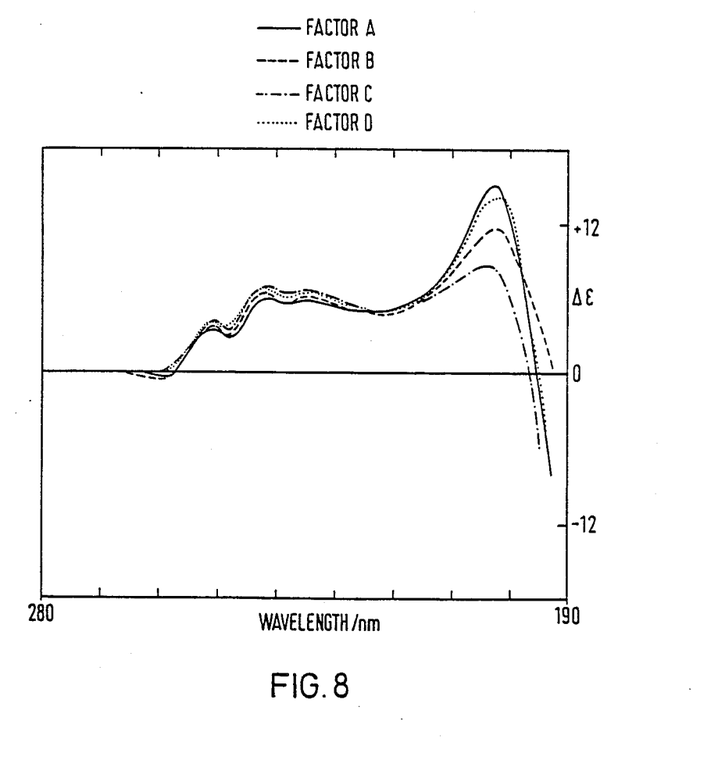

(vii) Circular dichroism curves for Factors A, B, C and D (ca. 0.1% solutions in methanol) are shown in FIG. 8. The curves are closely comparable in the region 230 to 260 nm associated with absorption of the diene chromophore. This indicates that the absolute configurations at $C_2$, $C_7$, $C_{17}$ and $C_{19}$ are the same in all four Factors.

The following are examples of formulations according to the invention. The term 'Active Ingredient' as used hereinafter means a compound of the invention and may be for example one of Factors A, B, C, D, E or F.

| Multidose parenteral injection | | |
|---|---|---|
|  | % w/v | Range |
| Active Ingredient | 4.0 | 1–5% w/v |
| Benzyl alcohol | 2.0 |  |
| Glyceryl triacetate | 30.0 |  |
| Propylene glycol    to | 100.0 |  |

Dissolve the active ingredient in the benzyl alcohol and glyceryl triacetate. Add propylene glycol and make up to volume. Filter the solution to remove any particulate contamination. Aspectically fill the product into injection vials and close with rubber seals or plugs held in position by aluminium overseals. Terminally sterilise the product by heating in an autoclave.

| Aerosol spray | % w/w | Range |
|---|---|---|
| Active Ingredient | 0.1 | 0.01–0.50% w/w |
| Trichloroethane | 29.9 | |
| Trichlorofluoromethane | 35.0 | |
| Dichlorodifluoromethane | 35.0 | |

Mix the Active Ingredient with trichloroethane and fill into the aerosol container. Purge the headspace with the gaseous propellant and crimp the valve into position. Fill the required weight of liquid propellant under pressure through the valve. Fit with actuators and dust-caps.

| Tablet Method of manufacture - wet granulation | | mg |
|---|---|---|
| Active Ingredient | | 250.0 |
| Magnesium stearate | 1% w/w | 4.5 |
| Maize starch | 5% w/w | 22.5 |
| Sodium starch glycolate | 2% w/w | 9.0 |
| Sodium lauryl sulphate | 1% w/w | 4.5 |
| Microcrystalline cellulose | to tablet core weight of 450 mg | |

Add sufficient quantity of a 10% starch paste to the active ingredient to produce a suitable wet mass for granulation. Prepare the granules and dry using a tray or fluid-bed drier. Sift through a seive, add the remaining ingredients and compress into tablets.

If required, film coat the tablet cores using hydroxypropylmethyl cellulose or other similar film-forming material using either an aqueous or non-aqueous solvent system. A plasticizer and suitable colour may be included in the film-coating solution.

| Veterinary tablet for small/domestic animal use Method of manufacture - dry granulation | mg |
|---|---|
| Active Ingredient | 50.0 |
| Magnesium stearate | 7.5 |
| Microcrystalline cellulose to tablet core weight of | 75.0 |

Blend the active ingredient with the magnesium stearate and microcrystallise cellulose. Compact the blend into slugs. Break down the slugs by passing through a rotary granulator to produce free-flowing Tablets. Compress into tablets.

The tablet cores can then be film-coated, if desired, as described above.

| Veterinary intrammary injection | | mg/dose | Range |
|---|---|---|---|
| Active Ingredient | | 150 mg | 150–500 mg |
| Polysorbate 60 | 3.0% w/w | | to 3 or 5 g |
| White Beeswax | 6.0% w/w | to 3 g | to 3 or 5 g |
| Arachis oil | 91.0% w/w | | to 3 or 5 g |

Heat the arachis oil, white beeswax and polysorbate 60° to 160° C. with stirring. Maintain at 160° C. for two hours and then cool to room temperature with stirring. Aseptically add the active ingredient to the vehicle and disperse using a high speed mixer. Refine by passing through a colloid mill. Aseptically fill the product into sterile plastic syringes.

| Veterinary oral drench | % w/v | Range |
|---|---|---|
| Active Ingredient | 0.35 | 0.05–0.50% w/v |
| Polysorbate 85 | 5.0 | |
| Benzyl alcohol | 3.0 | |
| Propylene glycol | 30.0 | |
| Phosphate buffer | as pH 6.0–6.5 | |
| Water | to 100.0 | |

Dissolve the active ingredient in the Polysorbate 85, benzyl alcohol and the propylene glycol. Add a proportion of the water and adjust the pH to 6.0–6.5 with phosphate buffer, if necessary. Make up to final volume with the water. Fill the product into the drench container.

| Veterinary oral paste | % w/w | Range |
|---|---|---|
| Active Ingredient | 7.5 | 1–10% w/w |
| Saccharin | 25.0 | |
| Polysorbate 85 | 3.0 | |
| Aluminium distearate | 5.0 | |
| Fractionated coconut oil | to 100.0 | |

Disperse the aluminium distearate in the fractionated coconut oil and polysorbate 85 by heating. Cool to room temperature and disperse the saccharin in the oily vehicle. Dispense the active ingredient in the base. Fill into plastic syringes.

| Granules for veterinary in-feed administration | % w/w | Range |
|---|---|---|
| Active Ingredient | 2.5 | 0.05–5% w/w |
| Limestone flour | to 100.0 | |

Blend the Active Ingredient with the limestone flour. Prepare the granules using a wet granulation process. Dry using a tray or fluid-bed drier. Fill into the appropriate container.

| Emulsifiable Concentrate | |
|---|---|
| Active ingredient | 50 g |
| Anionic emulsifier (e.g. Phenyl sulphonate CALX) | 40 g |
| Non-ionic emulsifier (e.g. Syperonic NP13) | 60 g |

Aromatic solvent (e.g. Solvesso 100) to 1 liter. Mix all ingredients, stir until dissolved.

| Granules | |
|---|---|
| (a) Active ingredient | 50 g |
| Wood resin | 40 g |
| Gypsum granules (20–60 mesh) to 1 kg (e.g. Agsorb 100 A) | |
| (b) Active ingredient | 50 g |
| Syperonic NP13 | 40 g |
| Gypsum granules (20–60 mesh) to 1 kg. | |

Dissolve all ingredients in a volatile solvent e.g. methylene chloride, add to granules tumbling in mixer. Dry to remove solvent.

The activity of Factors A, B, C, D, E and F was determined using a variety of pests and their hosts including the following: *Tetranychus urticae* (French bean and Myrobalan B plum), *Myzus persicae* (Chinese cabbage and radish), *Heliothis virescens* (cotton), *Chilo portellus* (Rape bean) *Meloidogyne incognita* (Mung bean), *Panonchus ulmi* (Myrobalan B plum), *Phorodon humuli* (hop), *Aulacorthum circumflexum* (cyclamen).

The product was used in the form of a liquid preparation. The preparations were made by dissolving the product in acetone. The solutions were then diluted with water containing 0.1% or 0.01% by weight of a wetting agent until the liquid preparations contained the required concentration of the product.

The test procedure adopted with regard to each pest comprised supporting a number of the pests on a medium which was usually a host plant and treating the medium with the preparation (residual test). In the case of *Tetranychus urticae* both the pests and the medium were treated with the preparation (contact test).

Following this procedure Factors A to F were found to be effective at concentrations (by weight of product) of 500 parts per million or less.

We claim:

1. A process for the preparation of a compound having a formula (III)

or mixtures thereof, in which $R^1$ is a methyl, ethyl or isopropyl group and $R^2$ is hydrogen or a methyl group; which comprises the step of cultivating a microorganism which is *Streptomyces thermoarchaensis* NCIB 12015, 12111, 12112, 12113 or 12114.

2. A process as claimed in claim 1 in which at least one compound of formula (III) is separated from the fermentation broth.

3. A process as claimed in claim 2 in which the mycelia of the microorganism are contacted with 4. A process as claimed claim 1 in which an individual compound of formula (III) is isolated.

5. A process as claimed in claim 1 in which $R^1$ is an isopropyl group and $R^2$ is hydrogen.

6. A process as claimed in claim 1 in which $R^1$ is a methyl group and $R^2$ is hydrogen.

7. A process as claimed in claim 1 in which $R^1$ is an ethyl group and $R^2$ is hydrogen.

8. A process as claimed in claim 1 in which $R^1$ is an isopropyl group and $R^2$ is a methyl group.

9. A process as claimed in claim 1 in which both $R^1$ and $R^2$ are methyl groups.

10. A process as claimed in claim 1 in which $R^1$ is an ethyl group and $R^2$ is a methyl group.

11. A process as claimed in claim 1 in which the compound having formula (III) is obtained in admixture with at least one other compound as claimed in said claim.

12. A process as claimed in claim 11 in which $R^2$ in formula (III) is hydrogen.

13. A process as claimed in claim 11 in which $R^2$ in formula (III) is a methyl group.

* * * * *